United States Patent [19]  
Smith et al.

[11] 4,012,448  
[45] Mar. 15, 1977

[54] SYNTHESIS OF ADRIAMYCIN AND 7,9-EPIADRIAMYCIN

[75] Inventors: Thomas H. Smith, East Palo Alto; Allan N. Fujiwara, Sunnyvale; David W. Henry, Menlo Park; William W. Lee, Palo Alto, all of Calif.

[73] Assignee: Stanford Research Institute, Menlo Park, Calif.

[22] Filed: Jan. 15, 1976

[21] Appl. No.: 649,225

[52] U.S. Cl. .......................... 260/591; 260/465 F; 260/473 F; 260/345.9; 260/487
[51] Int. Cl.² ........................................ C07C 49/82
[58] Field of Search ............... 260/590 FB, 591

[56] References Cited
UNITED STATES PATENTS

| | | | |
|---|---|---|---|
| 3,019,260 | 1/1962 | McCormick et al. | 260/590 |
| 3,102,914 | 9/1963 | Wilkinson et al. | 260/590 |
| 3,590,028 | 6/1971 | Arcamone et al. | 260/310 |
| 3,803,124 | 4/1974 | Arcamone et al. | 260/396 |
| 3,862,225 | 1/1975 | Conover et al. | 260/590 |

OTHER PUBLICATIONS

Arcamone et al., Gazny Chimie Ital., vol. 100, 11, pp. 949–980 (1970).
Arcamone et al., J.A.C.S., vol. 86, pp. 5334–5335.

*Primary Examiner*—Bernard Helfin
*Assistant Examiner*—James H. Reamer
*Attorney, Agent, or Firm*—Donovan J. De Witt

[57] ABSTRACT

A process for the synthesis of adriamycin and 7,9-epiadriamycin, both active antineoplastic agents, in which 7-deoxydaunomycinone, in either the 9s or racemic (±) form, is employed as the starting material, the process in one embodiment also being productive of the useful intermediate compound 4-methoxy-6,11-dihydroxy-7,8-dihydro-5,9(10H),12-naphthacenetrione. The process involves converting 7-deoxydaunomicinone successively to daunomycinone, adriamycinone, 14-0-p-anisyldiphenylmethyladriamycinone and finally to adriamycin or to both adriamycin and 7,9-epiadriamycin. When producing the latter mixture of diastereomers, the 7-deoxydaunomycinone starting material is first converted to racemate form by a process involving the successive production of 7-deoxydaunorubicinol, 4-methoxy-6,11-dihydroxy-7,8-dihydro-5,9(10H), 12-naphthacenetrione, (±)-4-methoxy-9-cyano-6,9,11-trihydroxy-7,8,9,10-tetrahydro-5,12-naphthacenedione, (±)-4-methoxy-9-cyano-9-(2'-tetrahydropyranyloxy)-6,11-dihydroxy-7,8,9,10-tetrahydro-5,12-naphthacenedione and (±)-7-deoxydaunomycinone.

1 Claim, No Drawings

SYNTHESIS OF ADRIAMYCIN AND 7,9-EPIADRIAMYCIN

ORIGIN OF INVENTION

The invention described herein was made in the course of or under contract with the National Cancer Institute, Department of Health, Education and Welfare.

PRIOR ART

U.S. Pat. Nos. 3,590,028 dated June 29, 1971 and 3,803,124 dated Apr. 9, 1975 to Arcamone et al. disclose methods for preparing adriamycin.

SUMMARY OF INVENTION

The invention relates in part to the discovery of a novel process for the synthesis of adriamycin (I) from the previously reported compound 7-deoxydaunomycinone (II) (Arcamone et al., J. Am. Chem. Soc. 86, 5335 (1964)), as well as to a novel process for the synthesis from (II) of the racemic mixture (±) 7-deoxydaunomycinone. The latter can be employed to prepare a mixture of the diastereomers adriamycin and 7,9-epiadriamycin. The invention also relates to the provision of the novel compounds 4-methoxy-6,11-dihydroxy-7,8-dihydro-5,9 (10H), 12-naphthacenetrione (IV), (±)-4-methoxy-9-cyano-6,9,11-trihydroxy-7,8,9,10-tetrahydro-5,12-naphthacenedione (V), (±)-4-methoxy-9-cyano-9-(2'-tetrahydropyranyloxy)6,11-dihydroxy-7,8,9,10-tetrahydro-5,12-naphthacenedione (VI), and 14-0-p-anisyldiphenymethyladriamycinone (XII).

Adriamycin is a clinically useful antineoplastic agent having a broad spectrum of activity. 7,9-epiadriamycin is potentially useful for this same purpose. The novel compounds IV – VI and XII presented structurally below, along with I, II and III (7-deoxydaunorubicinol) are useful intermediates in syntheses leading to the production of the said adriamycin compounds.

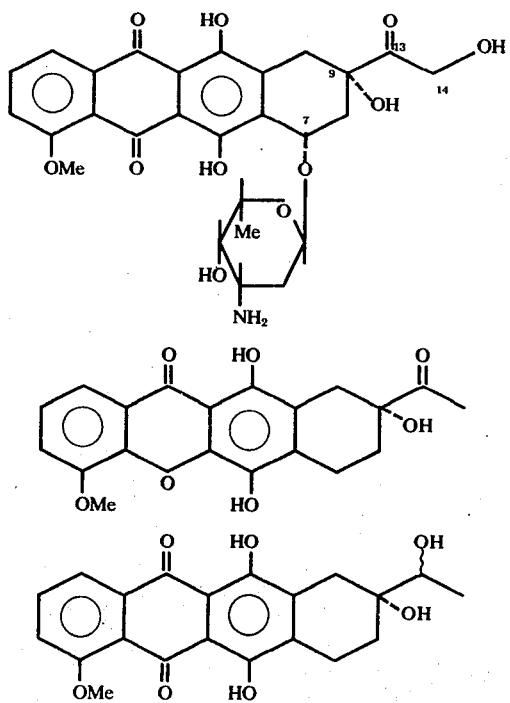

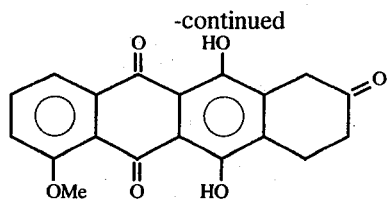

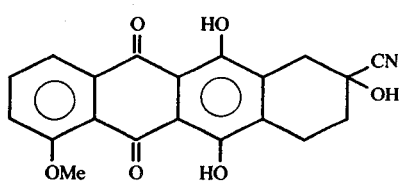

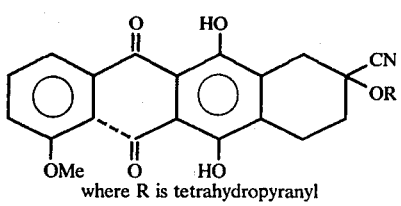

where R is tetrahydropyranyl

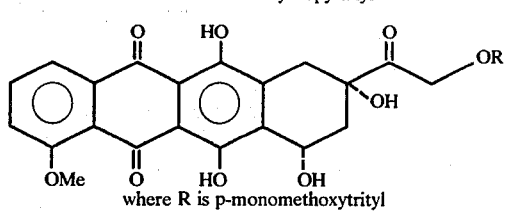

where R is p-monomethoxytrityl

The novel compounds of the present invention (IV-VII) can generically be described as the group having the structure

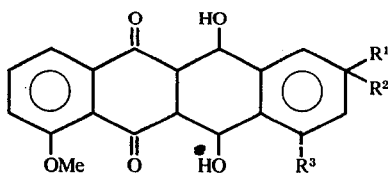

where $R^1$ represents p-monomethoxytrityloxyacetyl when $R^2$ represents α-hydroxyl, wherein $R^1$ and $R^2$ collectively represent oxo, wherein $R^1$ represents cyano when $R^2$ represents hydroxyl or tetrahydropyranyloxy group, and wherein $R^3$ represents hydrogen except when $R^2$ is p-monomethoxytrityloxyacetyl, in which case $R^3$ is hydroxyl.

In our operations the previously reported 7-deoxydaunomycinone (II) starting material, for convenience, was prepared by the reductive cleavage of daunorubicin. More specifically to daunorubicin hydrochloride (5.0 g, 8.87 mmole) in tetrahydrofuran (THF) (400 ml)/MeOH (120 ml) under $N_2$ was added $Na_2S_2O_4$ (3.09 g, 17.8 mmole) and $NaHCO_3$ (5.96 g, 71.0 mmole) in $H_2O$ (120 ml) over 5 min. The mixture was stirred for 15 min at 23°, poured into ice water (250 ml) and extracted with $CH_2Cl_2$ (8 × 75 ml). The extracts were combined, dried over $Na_2SO_4$ and evaporated to afford 3.85 g (99%) of (I): mp 229°–231°; ir$_{nujol}$ 2.85 (OH), 5.85 (C = O), 6.19, 629 μ (chelated quinone); pmr 100 MHz CDCl$_3$ δ 1.95 (m, 2H, 8-H$_2$), 2.42 (s, 3H, Ac), 3.00 (m, 4H, 7-H$_2$ and 10-H$_2$), 3.84 (br, s, 1H, 9-OH), 4.10 (s, 3H, —OCH$_3$), 7.36 (dd, 1H, J = 8Hz and J = 1Hz, 3-H), 7.73 (t, 1H, J = 8Hz, 2-H), 7.99 (dd, 1H, J = 8Hz and J = 1Hz, 1-H), 13.37 (s, 1H, phenolic OH), 13.79(s, 1H, phenolic OH); ms 70 ev m/e (%), 383 (9), 382 M (33), 364 (6), 340 (21), 339 (100), 321 (13), 43 (13).

Anal. Calcd. for $C_{21}H_{18}O_7 \cdot \frac{1}{2}H_2O$: C, 64.45; H, 4.91. Found: C, 64.71; H, 4.75.

It has been discovered that racemic (±)-7-deoxydaunomycinone can be prepared from (II) by a process in which the 9-acetyl group of (II) is first reduced to afford 7-deoxydaunorubicinol (III). This reaction proceeds slowly at ambient temperatures in the presence of a suitable solvent such as THF and using a typical reducing agent, e.g., LiAlH(Ot-Bu)$_3$. This reduction step forms the subject of Example 1 below.

Compound III is then subjected to oxidative cleavage to produce the novel non-asymmetric tetracyclic ketone (IV) in excellent yield, the reaction proceeding at room temperatures using a typical oxidant such as NaIO$_4$ and a solvent such as THF/aq MeOH. This reaction is described in Example 2 which also provides data characterizing (IV).

Addition of HCN to IV is productive of the novel compound (V) (Example 3), the reaction proceeding in standard fashion (KCN, HOAc, EtOH/CHCl$_3$, 0° to 23°, 5 hr).

Compound V is then reacted with dihydropyran under reflux conditions in the presence of an acid catalyst and a suitable solvent, e.g., THF, to provide the novel tetrahydropyranyl ether (VI), as described in Example 4.

Compound VI is converted to the desired (±)-7-deoxydaunomycinone by treatment in a solvent medium with methylmagnesium iodide at moderately elevated temperatures, followed by conventional acid hydrolysis (Example 5).

It has been discovered that the 7-deoxydaunomycinone starting material (II) in either the 9s or the corresponding (±) racemic condition can be converted to adriamycin (or to a mixture of adriamycin and 7,9-epiadriamycin in the case of the racemate) by a method which involves introducing hydroxyl groups first at the 7- and then at the 14-position of (II). The 14-OH group is then protected by a suitable blocking group, following which the resulting compound is reacted with a suitably blocked 1-halodaunosamine to provide an α-glycoside which is then freed of its blocking groups to provide adriamycin (or a mixture of adriamycin and 7,9-epiadriamycin) which is identical with the natural product.

For the sake of convenience, the method of the present invention for converting (II) to adriamycin will hereinafter be described as it relates to an operation wherein 7-deoxydaunomycinone in the 9s form is employed as the starting material. However, the same procedures can be practiced when proceeding from the racemate to a mixture of adriamycin and 7,9-epiadriamycin. More particularly, the method involves as the first step the introduction of a hydroxyl group at the 7-position of (II) by a synthesis route involving first a bromination step to form the 7-bromodaunomycinone (VII). (Br$_2$, 1.5 eq, in refluxing CCl$_4$, 4 hrs. with a free radical-initiating catalyst such as 2,2′-azobisisobutyronitrile (ABN)). The relatively unstable bromide compound, without isolation, may then be converted to the corresponding 7-epi trifluoroacetoxydaunomycinone (VIII) by reaction with NaOCOCF$_3$ in dimethyl sulfoxide (DMSO) (23°, 16 hrs). After aqueous workup and CHCl$_3$ extraction, the crude compound (VIII) is then equilibrated in trifluoroacetic acid and methanolized with CH$_3$OH/THF to provide daunomycinone (IX) which is recovered as the reaction mixture is poured into water and extracted with CHCl$_3$, the extracts being dried and then evaporated. These various steps leading from (VII) to (IX) are set forth more particularly below in Example 6.

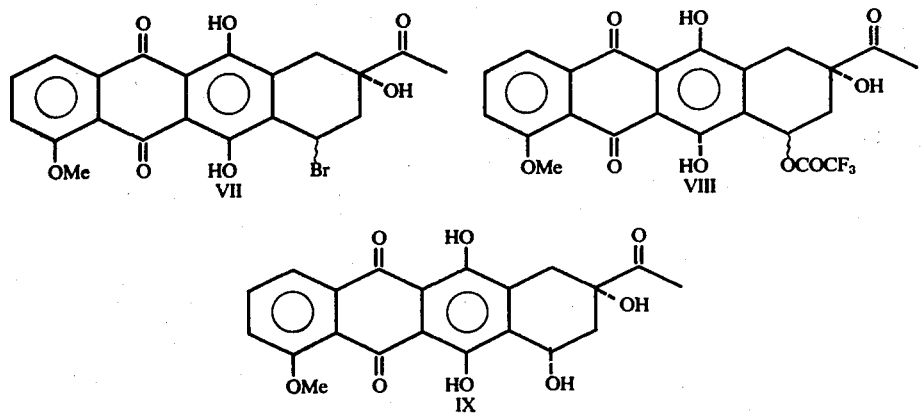

In order to introduce a hydroxyl group at the 14-position of compound (IX), said position is first provided with a bromine atom in conventional bromination step (Br$_2$, CHCl$_3$, 23°, 16 hrs). The 14-bromodaunomycinone (X), after being freed of CHCl$_3$, is dissolved in aqueous acetone and subjected to hydrolysis with NaOH (1.1 eq, reflux 5 mins) to afford adriamycinone (XI) which is recovered after water workup and extraction with CHCl$_3$/MeOH. This portion of the process forms the subject of Example 7.

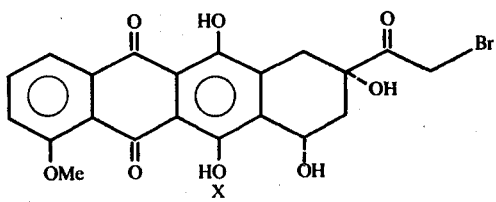 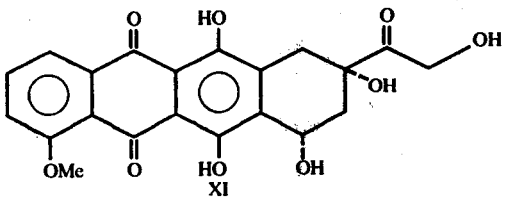

The 14-hydroxyl group in compound (XI) is then protected by the introduction of a suitable blocking group. A preferred practice is to react (XI) with p-anisylchlorodiphenylmethane (10 eq) in a pyridine solvent at low temperatures for an extended reaction period, typically 5° C for 116 hrs. The resulting 14-0-p-anisyldiphenylmethyladriamycinone product (XII) is recovered after water workup and extraction with CHCl$_3$, followed by crystallization from CHCl$_3$/pet. ether. The foregoing reaction is described more fully in Example 8.

The protected algycone (XII) is now reacted with a suitably blocked 1-halodaunosamine under Koenigs-Knorr conditions to provide an α-glycoside. A preferred sugar reactant for this purpose is 1-bromo-N-trifluoroacetyl-0-p-nitrobenzoyldaunosamine (XIII). Reaction of the latter compound with (XII) (50°, 70 hr in the presence of mercuric cyanide, mercuric bromide and powder molecular sieve material (3A)) affords the glycoside (XIV). The unpurified (XIV) product is deacylated with dilute caustic in aqueous THF at 0° to afford the glycoside (XV) which is deblocked as regards to the sugar moiety. Compound (XV) can be separated from the water-soluble sugar by-products of the coupling reaction by partitioning the reaction mixture between CHCl$_3$ and water. Finally, treatment of (XV) with dilute HCl in THF at 5° for several hours detritylates (XIV) and affords adriamycin.HCl (XVI) which is identical with the natural product. Recovery of (XVI) can be effected as the reaction mixture is concentrated and lyophilized, the residue being partitioned between water and CH$_2$Cl$_2$, and the aqueous layer being lyophilized to afford (XVI) in good yield. The procedures described in this paragraph are set forth in detail in Example 9.

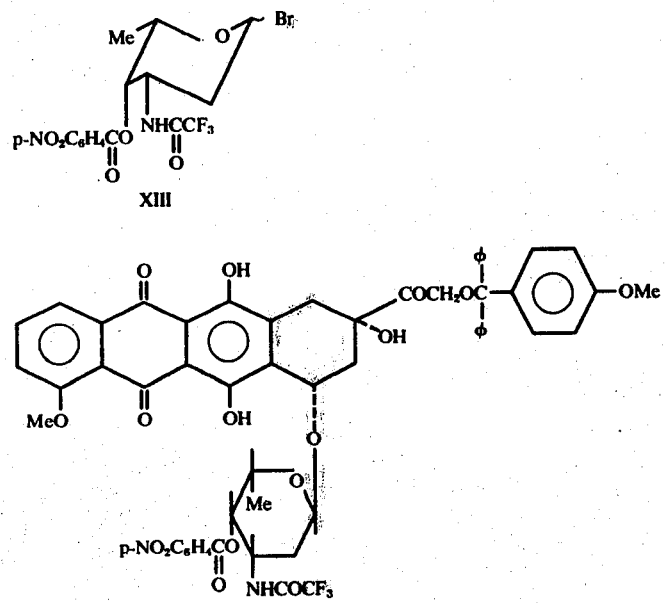

14-0-p-anisyldiphenylmethyl-4'-0-p-nitrobenzoyl-3'-N-trifluoroacetyladriamycin XIV,

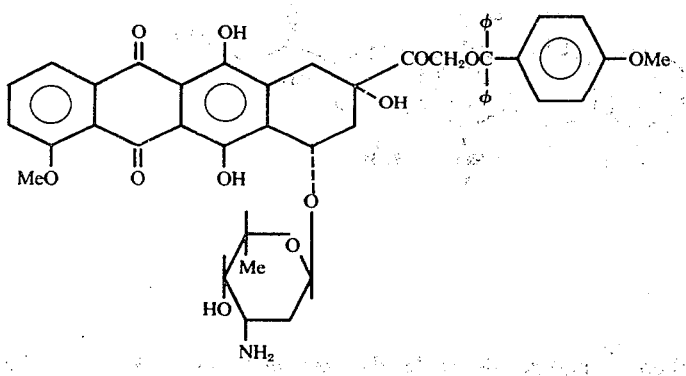

14-O-p-anisyldiphenylmethyladriamycin XV

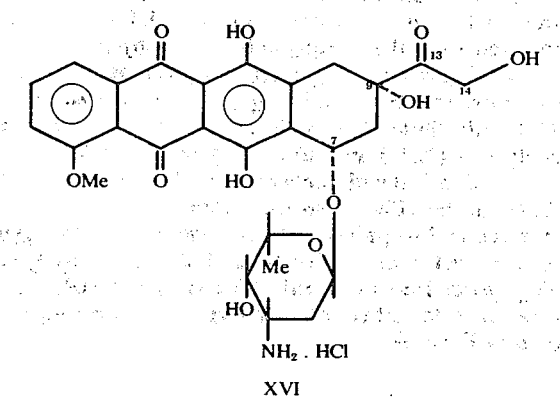

XVI

The following examples illustrate the invention but are not to be construed as limiting the same.

EXAMPLE 1

7-Deoxydaunorubicinol (III). 7-Deoxydaunomycinone (II), (300 mg, 0.79 mmole) and LiAl (Ot-Bu)$_3$ H (480 mg, 1.85 mmole) were stirred in THF (30 ml) under N$_2$ for 6 hr. Additional LiAl (Ot-Bu)$_3$ H (120 mg) was added and after 16 hrs a third portion of LiAl (Ot-Bu)$_3$ H (240 mg) was introduced. After the last addition stirring was continued for 24 hr. The reaction mixture was poured into 2NHCl (50 ml) and heated on the steam bath for 1 hr. The mixture was allowed to cool and extracted with CH$_2$Cl$_2$ (3 × 40 ml). The extracts were combined, dried over Na$_2$SO$_4$ and evaporated. The residue was recrystallized from CH$_2$Cl$_2$/CHCl$_3$ to afford 161.6 mg of (III). The mother liquors were evaporated and the residue chromatographed (plc-silica gel, 93.7 CHCl$_3$/MeOH) to afford 35.4 mg of starting material (II) and an additional 79.5 mg of (III). Combined yield 240.1 mg (80%) of (III): mp 230°–233°; ir$_{nujol}$ 2.85 (OH), 6.20, 6.50 μ (chelated quinone); ms 70 ev m/e (%), 385 (18), 384 M (94), 340 (25), 339 (100).

Anal. Calcd for C$_{21}$H$_{20}$O$_7$: C, 65.61; H, 5.25. Found: C, 65.28; H, 5.39.

EXAMPLE 2

4-Methoxy-6,11-dihydroxy-7,8-dihydro-5,9(10H), 12-naphthacenetrione (IV). To 7-deoxydaunorubicinol (III), (377.6 mg, 0.98 mmole) in THF (60 ml) was added NaIO$_4$ (462 mg, 2.16 mmole) in 50% aq MeOH (2 ml). The solution was stirred under N$_2$ for 16 hr at 23°. The reaction mixture was concentrated to approximately 10 ml and extracted with CH$_2$Cl$_2$ (2 × 30 ml). The extracts were combined, dried over Na$_2$SO$_4$ and evaporated. The residue was chromatographed (40 g silica gel, 98:2 CHCl$_3$/MeOH) to afford in order of elution 237.2 mg (99% yield, 71% conversion) of (IV): ir$_{nujol}$ 5.82 (C = O), 6.15, 6.35 μ (chelated quinone); pmr 100 MHz CDCl$_3$ δ 2.64 (t, 2H, 8-H$_2$), 3.26 (t, 2H, 7-H$_2$), 3.63 (s, 2H, 10-H$_2$), 4.09 (s, 3H, OMe), 7.38 (dd, 1H, J = 8 Hz and J = 1Hz, 3-H), 7.77 (t, 1H, J = 8Hz, 2-H), 8.04 (dd, 1H, J = 8Hz and J = 1-H), 13.30 (s, 1H, phenolic OH), 13.80 (s, 1H, phenolic OH); ms 12 ev m/e (%) 338 M (100).

Anal. Calcd for C$_{19}$H$_{14}$O$_6$·½H$_2$O: C, 65.7; H, 4.35. Found: C, 66.1; H, 4.49.

Further elution afforded 110.6 mg of starting material (III).

EXAMPLE 3

(±)-4-Methoxy-9-cyano-6,9,11-trihydroxy-7,8,9,10-tetrahydro-5,12-naphthacenedione (V). 4-Methoxy-6,11-dihydroxy-7,8-dihydro-5,9 (10H),12-naphthacenetrione (IV) (45.3 mg, 0.134 mmole) and KCN (300 mg) were placed in 50% CHCl$_3$/EtOH (8 ml) and cooled to 0°. HOAc (0.4 ml) was added and the mixture was stirred at 23° for 5 hr. The reaction mixture was diluted with H$_2$O (15 ml), the organic phase separated and the aqueous phase extracted with CHCl$_3$ (10 ml). The organic solutions were combined, dried over Na$_2$SO$_4$ and evaporated. The residue was chromatographed (8 g silica gel, 98.2 CHCl$_3$/MeOH) to afford 38.0 mg (77%) of (V): mp 232°–235° (dec); ir$_{nujol}$ 2.93 (OH), 6.20, 6.31 μ (chelated quinone); pmr 100 MHz CDCl$_3$ δ 2.1–2.4 (m, 2H, 8-H$_2$), 2.8–3.4 (m, 5H, benzylic H's and 9-OH), 4.08 (s, 3H, OMe), 7.36 (dd, 1H, J = 8Hz and J = 1Hz, 3-H), 7.74 (t, 1H, J = 8Hz, 2-H), 7.99 (dd, 1H, J = 8Hz and J = 1Hz, 1-H), 13.28 (s, 1H, phenolic OH), 13.68 (s, 1H, phenolic OH); ms 12 ev m/e (%) 338 M-HCN (100).

EXAMPLE 4

(±)-4-Methoxy-9-cyano-9-(2'-tetrahydropyranyloxy)-6,11-dihydroxy-7,8,9,10-tetrahydro-5,12-naphthacenedione (VI).

(±)-4-Methoxy-9-cyano-6,9,11-trihydroxy-7,8,9,10-tetrahydro-5, 12-naphthacenedione (V), (37.0 mg, 0.11 mmole) was placed in 50% dihydropyran/THF (10 ml) with conc HCl (1 drop) and the solution was refluxed for 5 hr. Pyridine (2 ml) was added and the solvents removed. The residue was dissolved in CHCl$_3$ (10 ml), washed with H$_2$O (3 ml) and dried over Na$_2$-

SO₄. The solvent was removed and the residue was crystallized from CHCl₃/pet. ether (30°-60°) to afford 36.9 mg (90%) of (VI): mp 204°-206°; ir$_{nujol}$ 6.20; 6.30 μ (chelated quinone); pmr 100 MHz CDCl₃ δ 1.64 (m, 6H, 3', 4',5'-H's), 2.32 (m, 2H,8-H₂), 3.05 (m, 2H, 10-H₂), 3.34 (t, 2H, 7-H₂), 3.58 (m, 2H, 6'-H₂), 4.10 (s, 3H, OMe), 5.18 (m, 1H, 2'-H), 7.35 (dd, 1H, J = 8Hz and J = 1Hz, 3-H), 7.75 (t, 1H, J = 8Hz, 2-H), 8.02 (dd, 1H, J = 8Hz and J = 1Hz, 1-H), 13.40 (s, 1H, phenolic OH), 13.76 (d, 1H, phenolic OH).

Anal. Calcd for C₂₅H₂₃O₇N: C, 66.80; H, 5.16; N, 3.11. Found: 3, 66.70; H, 5.25; N, 3.14.

EXAMPLE 5

(±)-7-Deoxydaunomycinone.

Methylmagnesium iodide (0.4 ml of 2.5 M soln in ether, 1.00 mmole) was added under N₂ to a stirred solution of (±)-4-methoxy-9-cyano-9-(2'-tetrahydropyranyloxy)-6,11-dihydroxy-7,8,9,10-tetrahydro-5,12-naphthacenedione (VI), (15mg, 0.033 mmole) in THF (1.5 ml). The mixture was stirred at 23° for 4 hr and at 55° for 10 hr. The reaction was quenched with 60% HOAc (10 ml) and the solution was heated on a steam bath for 45 min. The mixture was diluted with water (10 ml), extracted with CHCl₃ (2 × 10 ml). The extracts were combined, washed and saturated NaHCO₃ (5 ml), dried over Na₂SO₄ and evaporated. The residue was chromatographed (plc-silica gel, 85:15 CHCl₃/EtOAc) and crystallized from CHCl₃/pet. ether (30°-60°) to afford 5.7 mg (45%) of (VII): mp 230°-232°; ir$_{nujol}$ 2.85 (OH), 5.82 (C=O), 6.20, 6.30 μ (chelated guinone); pmr 100 MHz CDCl₃ δ 1.95 (m, 2H, 8-H₂), 2.42 (s, 3H, Ac), 3.00 (m, 4H, benzylic H's), 3.74 (br.s, 1H, 9-OH), 4.10 (s, 3H, OMe), 7.36 (dd, 1H, J = 8Hz and J - 1Hz, 3-H), 7.73 (t, 1H, J = 8Hz, 2-H), 7.99 (dd, 1H, J = 8Hz and J = 1Hz, 1-H), 13.37 (s, 1H, phenolic OH), 13.79 (s, 1H, phenolic OH).

Anal. Calcd for C₂₁H₁₈O₇.½H₂O: C, 64.45; H, 4.91. Found: 3, 64.14; H, 4.56.

EXAMPLE 6

Daunomycinone (IX).

7-Deoxydaunomycinone (II), (100 mg. 0.262 mmole), Br₂ (3.0 ml of 0.125 M soln in CCl₄, 0.375 mmole) and ABN (6.4 mg, 0.04 mmole) were placed in CCl₄ (20 ml) under N₂ and refluxed for 3 hr. Additional Br₂ (0.19 mmole) was introduced and refluxing was continued for another hour. The solvent was removed and the residue was placed in DMSO (20 ml) with NaOCOCF₃ (200 mg) and stirred under N₂ for 16 hr. The reaction mixture was poured into H₂O (50 ml) and extracted with CHCl₃ (3 × 15 ml). The extracts were combined, washed with H₂O (10 ml) and saturated NaCl (10 ml), dried over Na₂SO₄ and evaporated. The residue was dissolved in TFA (10 ml) and stirred at 23° for 1.5 hr. The solvent was removed and the residue dissolved in 4:1 MeOH/THF (20 ml) and stirred at 23° for 4 hr. The solution was poured into H₂O (50 ml) and extracted with CHCl₃ (3 × 15 ml). The extracts were combined, dried over Na₂SO₄ and evaporated. The residue was chromatographed [E. Merck, silica gel 60 prepacked column (size B), 99:1 to 97:3 CH₂Cl₂/MeOH] to afford in order of elution 17.7 mg (18%) of II, 37.0 mg (35%) of IX: mp 215°-217°; ir$_{nujol}$ 2.90 (OH), 5.85 (C=O), 6.20, 6.31 μ (chelated quinone); pmr 100 MHz CDCl₃ δ 2.05-2.35 (m, 2H, 8-H₂), 2.48 (s, 3H, Ac), 2.93 (d, 1H, J = 19Hz, 10α-H), 3.25 (d, 1H, J = 19Hz, 10β-H), 3.68 (s, 1H, 9-OH), 4.14 (s, 3H, OMe), 4.53 (s, OH, 7-OH), 5.36 (m, 1H, ½ = 7Hz, 7-H), 7.40 (dd, 1H, J = 8Hz and J = 1Hz, 3-H), 7.79 (t, 1H, 6-OH), 14.07 (s, 1H, 11-OH).

Anal. Calcd for C₂₁H₁₈O₈. H₂O: C, 60.58; H, 4.85. Found: C, 60.96; H, 4.45.

Continued elution afforded 6.1 mg (6%) of 7-epidaunomycinone: mp 218°-220°; ir$_{nujol}$ 2.85 (OH), 5.85 (C=O), 6.20, 6.30 μ (chelated quinone); pmr 100 MHz CDCl₃ δ 2.2-2.5 (m, 2H, 8-H₂), 2.40 (s, 3H, Ac), 2.90 (d, 1H, J = 17Hz, 10α-H), 3.16 (d, 1H, 10β-H), 3.82 (s, 1H, 9-OH), 4.09 (s, 3H, OMe), 4.33 (d, 1H, 7-OH), 5.37 (m, 1H, ½ = 17Hz, 7-H), 7.40 (dd, 1H, J = 8Hz and J = 1Hz, 3-H), 7.79 (t, 1H, J = 8Hz, 2-H), 8.06 (dd, 1H, J = 8Hz and J = 1Hz, 1-H), 13.26 (s, 1H, 6-OH), 14.33 (s, 1H, 11-OH); ms 12 ev m/e (%) 399 (22), 398 M (87), 380 (56), 362 (45), 355 (17), 339 (15), 338 (64), 337 (100).

Anal. Calcd for C₂₁H₁₈O₈.¼H O: C, 62.61; H, 4.64. Found: C, 62.68; H, 4.51.

EXAMPLE 7

Adriamycinone (XI).

Daunomycinone (IX) (10 mg, 0.025 mmole) was placed in CHCl₃ (1 ml). Br₂ (13.5 mg) in CHCl₃ (0.25 ml) was added and the solution stirred at 23° for 16 hrs. The solvent was removed and the residue was dissolved in 80% aq acetone (5 ml). NaOH (1.1 mg. 0.028 mmole) was added and the blue solution was refluxed for 5 min when the red color returned. The solution was concentrated to approximately 2 ml, diluted with water (10 ml) and extracted with 50% CHCl₃/MeOH (3 × 10 ml). The extracts were combined, dried and evaporated. The residue was crystallized from CHCl₃-MeOH/pet. ether (30°-60°) to afford 9.0 mg (87%) of (XI): ir$_{nujol}$ 2.85 (OH), 5.75 (C=O), 615, 628 μ (chelated quinone); pmr 100 MHz CDCl₃ δ 2.0-2.5 (m, 2H, 8-H₂), 2.8-3.2 (m, 2H, 10-H₂), 3.43 (m, 1H, 9-OH), 4.09 (s, 3H, OMe), 4.70 (d, 2H, J = 16Hz, 14-H₂), 5.34 (m, 1H, ½ = 8Hz, 7-H), 7.38 (dd, 1H, J = 8Hz and J = 1Hz, 3-H), 7.76 (t, 1H, J = 8Hz, 2-H), 8.00 (dd, 1H, J = 8Hz and J = 1Hz, 1-H), 13.24 (s, 1H, 6-OH), 13.99 (s, 1H, 11-OH).

Anal. Calcd for C₂₁H₁₈O₉.1½H₂0: C, 59.57; H, 4.53. Found: C, 59.63; H, 4.54.

EXAMPLE 8

14-0-p-Anisyldiphenylmethyladriamycinone (XII).

Adriamycinone (XI), (369 mg, 0.90 mmole) was dissolved in pyridine (36 ml) and cooled to 5°. p-Anisylchlorodiphenylmethane (2.77 g, 90 mmole) was added in one portion, stirred well and the solution kept at 5° for 116 hr. The reaction mixture was poured into ice water (200 ml) and extracted with CHCl₃ (2 × 100 ml). The extracts were combined, washed with 3N H₂SO₄ (2 × 100 ml), saturated NaHCO₃ (100 ml) and water (100 ml), dried over Na₂SO₄ and evaporated. The residue was crystallized from CHCl₃/pet. ether (30°-60°) to afford 520 mg (94%) of (XII): mp 198°-203°; ir$_{nujol}$ 2.90 (OH), 5.78 (C=O), 6.20 6.30 μ (chelated quinone); pmr 60 MHz CDCl₃ δ 2.08 (m, 2H, 8-H₂), 2.78 (br. d, 2H, 10-H₂), 3.83 (s, 3H, Tr-OMe), 4.00 (s, 3H, 4-OMe), 4.52 (s, 2H, 14-H₂), 5.10 (m, 1H, ½ = 7Hz, 7-H), 6.8-7.8 (m, 17H, Ar-H's), 13.00 (s, 1H, 6-OH), 13.58 (s, 1H, 11-OH).

Anal. Calcd for $C_{21}H_{18}O_9 \cdot 1\tfrac{1}{2}H_2O$: C, 69.0; H, 5.23. Found: C, 69.1; H, 5.37.

EXAMPLE 9

Adriamycin.HCl (I).

14-0-p-Anisyldiphenylmethyladriamycinone (XII), (0.51 g, 0.742 mmole), Hg(CN)$_2$ (1.56 g), HgBr$_2$ (0.71 g) and powdered molecular sieve 3A (3.6 g) were placed in THF (75 ml) and refluxed for 2 hr. Six one molar equivalent portions of freshly prepared 1-bromo-N-trifluoroacetyl-0-p-nitrobenzoyldaunosamine were added at 0, 19, 28, 44, 50 and 70 hr. The bromosugar was prepared by bubbling anhy. HBr into a chilled solution of N-trifluoroacetyl-1,4-di-0-p-nitrobenzoyl-daunosamine (405 mg, 0.74 mmole) for 5 min. The solvent is removed, the residue is triturated with CH$_2$Cl$_2$ (10 ml) and filtered to remove the precipitated p-nitrobenoic acid. The filtrate is then added to the reaction mixture. Additional portions of Hg(CN)$_2$ (1.56 g), HgBr$_2$ (0.71 g) and powdered molecular sieve 3A (3.6 g) were added at 19 and 50 hrs. The total reaction time was 73.5 hr after which the reaction mixture was filtered and evaporated. The residue was triturated with CHCl$_3$ (100 ml), filtered, washed with 30% KI (2 × 50 ml), dried over Na$_2$SO$_4$ and evaporated.

The residue was dissolved in 1:1 0.1N NaOH/THF (60 ml) and stirred at 0° for 4.5 hr. The reaction mixture was acidified with 0.1N HCl and extracted with CHCl$_3$ (2 × 40 ml). The pH of the aqueous phase was adjusted to 9.5 with 01N NaoH. The aqueous phase was then extracted with 4:1 CHCl$_3$/MeOH (30 ml). The organic solutions were combined, washed with saturated NaHCO$_3$ (40 ml) and water (4 × 40 ml), dried over Na$_2$SO$_4$ and evaporated.

The residue was dissolved in THF (60 ml) and cooled to 0°. 0.1N HCl (60 ml) was added with stirring and the solution was kept at 5° for 18 hr. The solution was concentrated to approximately 50 ml and lyophilized. The residue was partitioned between water and CH$_2$Cl$_2$. The aq layer was lyophilized to afford 156 mg (37%) of adriamycin.HCl (XVI).

We claim:

1. The compound which is 4-methoxy-6,11-dihydroxy-7,8-dihydro-5,9 (10H),12-naphthacenetrione.

* * * * *

UNITED STATES PATENT AND TRADEMARK OFFICE
CERTIFICATE OF CORRECTION

PATENT NO. : 4,012,448
DATED : March 15, 1977
INVENTOR(S) : Thomas H. Smith, et al.

It is certified that error appears in the above-identified patent and that said Letters Patent are hereby corrected as shown below:

Column 1, structure II, the second ring from the left, attach the lower oxygen atom to the ring with a double bond.

Column 2, line 40, erase the circle which appears in the fourth ring from the left and insert said circle into the third ring from the left.

Column 10, line 4, before "1/2" insert --$\nu$--.

Column 10, line 14, before "1/2" insert --$\nu$--.

Column 10, line 42, before "1/2" insert --$\nu$--.

Column 10, line 67, before "1/2" insert --$\nu$--.

The above errors were those of the PTO and the balance are those of applicants.

Column 2, structure VI, the second ring from the left, change the dotted line to a solid line.

Column 7, line 57, change "6.50" to --6.30--.

Column 8, line 48, change "98.2" to --98:2--.

Column 9, line 26, change "and" to --with--.

Column 9, line 30, change "VII" to --[$\pm$(II)]--.

Column 10, line 1, change "10$\alpha$-H)" to --10$\beta$-H)--

UNITED STATES PATENT AND TRADEMARK OFFICE
CERTIFICATE OF CORRECTION

PATENT NO. : 4,012,448
DATED : March 15, 1977
INVENTOR(S) : Thomas H. Smith, et al.

It is certified that error appears in the above-identified patent and that said Letters Patent are hereby corrected as shown below:

Column 10, line 2, change "10β-H" to --10α-H--.

Column 10, line 12, change "10α-H" to --10β-H--; same line change "10β-" to --10α---.

Column 10, line 20, change "1/4H O" to --1/4H$_2$O--.

Column 11, line 19, change "p-nitrobenoic" to --p-nitrobenzoic--

Signed and Sealed this sixteenth Day of August 1977

[SEAL]

Attest:

RUTH C. MASON
Attesting Officer

C. MARSHALL DANN
Commissioner of Patents and Trademarks